United States Patent [19]

Bartelsman et al.

[11] 4,455,370
[45] Jun. 19, 1984

[54] TRANSFERRING SEPARATED COMPONENTS IN GEL ELECTROPHORESIS VIA NYLON MEMBRANE

[75] Inventors: Bart W. Bartelsman, Canton, Mass.; Dennis L. Fost, Ridgewood, N.J.

[73] Assignee: E. I. Du Pont de Nemours and Company, Wilmington, Del.

[21] Appl. No.: 472,984

[22] Filed: Mar. 7, 1983

Related U.S. Application Data

[63] Continuation of Ser. No. 378,899, May 17, 1982, abandoned.

[51] Int. Cl.$^3$ .................. G01N 33/50; G01N 33/68; G01N 27/26
[52] U.S. Cl. .................. 435/6; 204/403; 435/172; 435/180; 435/172.3; 436/86; 436/94; 935/78
[58] Field of Search .................. 435/6, 172, 180; 436/531, 86, 94; 204/403

[56] References Cited

U.S. PATENT DOCUMENTS

| 2,783,894 | 3/1957 | Lovell et al. |
|---|---|---|
| 3,408,315 | 10/1968 | Paine |
| 3,553,067 | 1/1971 | Dwyer et al. |
| 3,594,263 | 7/1971 | Dwyer et al. |
| 3,759,773 | 9/1973 | Dwyer et al. |
| 3,843,324 | 10/1974 | Edelman .................. 436/531 |
| 3,876,738 | 4/1975 | Marinaccio et al. |
| 4,048,038 | 9/1977 | Kunkle |
| 4,106,920 | 8/1978 | Hughes et al. |
| 4,128,470 | 12/1978 | Kiratsuka et al. |

OTHER PUBLICATIONS

R. P. Legocki et al., Anal. Biochem., III, 385–392 (1981).
G. M. Edelman et al., Proc. Nat. Acad. Sci., 68(9), 2153–2157 (Sep. 1971).
Southern, Journal of Molecular Biology, 98, 503–517 (1975).
Reiser et al., Biochemical and Biophysical Res. Comm. 85, 1104–1112 (1978).
Singer, Journal of Biological Chemistry, 12, 5506–5514 (1979).
Thomas, Proceedings of the Nat'l Academy of Sci., USA, 77, 5201–5205 (1980).
Bittner et al., Analytical Biochemistry, 102, 459–471 (1980).
"Sequences" adv. brochure of Schleicher & Schuell, Inc. 1978.
Data Sheets 845-D and 845-F of Millipore Corporation, 1979.

*Primary Examiner*—Sidney Marantz

[57] ABSTRACT

Microporous nylon films used as transfer membranes for nucleic acids, proteins, bacteria and viruses.

10 Claims, No Drawings

TRANSFERRING SEPARATED COMPONENTS IN GEL ELECTROPHORESIS VIA NYLON MEMBRANE

CROSS REFERENCE TO RELATED APPLICATION

This application is a continuing application of Ser. No. 378,899 filed May 17, 1982, now abandoned.

BACKGROUND OF THE INVENTION

1. Field of the Invention

This invention relates to transfer and immobilization of nucleic acids, proteins, bacteria and viruses from electrophoresis gels or culture media to a porous membrane (film) for the purpose of probing the immobilized species for specific nucleic acids or proteins.

2. Description of the Prior Art

In a variety of procedures in analytical biochemistry it is necessary for the investigator to transfer a substance to be analyzed from a gel or culture medium to an immobilizing membrane for subsequent analysis.

In 1975, a method of transferring nucleic acids from electrophoresis gels to an adsorptive membrane was devised (Southern, E. M., *J. Molecular Biology,* 98, 503, (1975), and this general procedure is used widely in molecular biology laboratories. The Southern method involves placing filter paper on a glass plate elevated over a tray of buffer solution, with the ends of the paper extending into the buffer to form wicks; placing the gel containing the sample to be transferred on top of the filter paper; placing an adsorptive microporous membrane made of nitrocellulose on top of the gel; and placing paper towels on top of the membrane to blot the buffer and drive the sample into the membrane by capillary action. This is referred to as transfer by blotting.

In 1980, Bittner et al. (*Anal. Biochem.* 102, 459, (1980) described a modification in which an electrophoresis gel containing a sample to be transferred and an adsorptive nitrocellulose membrane are sandwiched between two sheets of filter paper, placed in an electrode cassette, immersed in a buffer solution, and subjected to an electrical potential. This is referred to as electrophoresis transfer or electroblotting.

Adsorptive microporous membranes have also been used to lift bacteria and viruses from growth media for subsequent manipulation and analysis of bacterial and viral nucleic acids and proteins.

Several materials have been used or suggested for use as transfer membranes, including nitrocellulose, nitrobenzyloxymethyl cellulose, aminobenzyloxymethyl cellulose, aminophenylthioether cellulose, diethylaminoethyl cellulose, and polyvinylidene fluoride.

Membranes of the cellulose-based materials are brittle and weak. They must be handled carefully in the transfer process. They cannot tolerate much of the manipulation involved in subsequent analytical work, such as hybridization of nucleic acids with radioactive probes, probe removal and rehybridization, immunological screening of proteins, lysis of cells, and autoradiography.

Microporous nylon films are used for filtration in many laboratories and industrial applications. Microporous nylon films have also been suggested (Hiratsuka et al. U.S. Pat. No. 4,128,470) for use as electrophoresis media in place of polyacrylamide gels in isoelectric focusing. Semi-permeable nylon membranes have been suggested for use in electroflocculation of suspended clay particles (Kunkle U.S. Pat. No. 4,048,038). Impermeable nylon films have been suggested as base sheets for microporous cellulose acetate or acetate/nitrate membrane electrophoresis media (Dwyer et al. U.S. Pat. Nos. 3,553,067, 3,594,263 and 3,759,773).

SUMMARY OF THE INVENTION

We have discovered that microporous adsorptive nylon films make excellent transfer membranes for nucleic acids, proteins, bacteria and viruses. Compared to the cellulose-based films previously used as transfer membranes, the nylon films are physically stronger and more resistant to the manipulative steps used in transfer and subsequent analysis. The nylon films are strong enough, for example, that multiple hybridization of DNA or RNA, (that is, hybridization with a radioactive probe, removal of the probe by denaturation, and rehybridization) can be performed on the same membrane. Nitrocellulose membranes typically are relatively fragile materials. Nylon is about equivalent to nitrocellulose in ability to bind the mentioned biological materials. In contrast to nitrocellulose, nylon can be efficiently used for the electrophoretic transfer of RNA from gels.

Accordingly, we regard as our invention an improvement in methods for transferring nucleic acids, proteins, bacteria or viruses from electrophoresis gels or culture media to an adsorptive, microporous transfer membrane, the improvement comprising the use of microporous adsorptive nylon film as the membrane.

The invention includes transfer of nucleic acids or proteins from an electrophoresis gel to a microporous adsorptive nylon membrane by blotting or electroblotting. It also includes transfer of nucleic acids, proteins, bacteria or viruses from culture media (including plaques) by contacting the substance to be transferred in the medium with a microporous adsorptive nylon membrane.

DETAILED DESCRIPTION

The microporous membrane used in this invention can be formed of any adsorptive nylon, i.e. any film-forming polyamide having an affinity for biological molecules. The membranes can be made by the processes disclosed in Lovell et al. U.S. Pat. No. 2,783,894 and Marinaccio et al. U.S. Pat. No. 3,876,738; pore size can be varied and controlled by methods disclosed in these patents. Pore size for these membranes is expressed in terms of bacterial filtration ratings. For example, ability to quantitatively remove the organism *Pseudomonas diminuta* is accepted as defining a $0.2\mu$ bacterial rated filter, and ability to quantitatively remove the organism *Serratia marcescens* is accepted as defining a $0.45\mu$ bacterial rated filter. Microporous membranes of 66-nylon (copolymer of hexamethylenediamine and adipic acid) are commercially available from AMF Inc., White Plains, N.Y. and Pall Corp., Glen Cove, N.Y. with bacterial filtration ratings of $0.1\mu$, $0.2\mu$, $0.45\mu$, $0.65\mu$, $0.8\mu$, $1.2\mu$, $3\mu$ and $5\mu$. Materials with bacterial filtration ratings in the range of about $0.2\mu$ to $0.8\mu$ are preferred, although materials with larger or smaller ratings can be used. For transfer of DNA smaller than about 1 kilobase and for RNA, the $0.2\mu$ rated materials are preferred. For the transfer of DNA molecules larger than about 1 kilobase, the $0.45\mu$–$0.8\mu$ rated materials are preferred. In contrast, pore size does not seem to be as important in the transfer and retention of protein molecules, bacteria or viruses.

For transferring bacteria, viruses, nucleic acids, or proteins from a culture medium by direct contact, the nylon membrane should be laminated to a support film, e.g. a polyethyleneterephthalate film, to prevent buckling. Alternatively, the membrane should be wet before contacting the medium.

Further details on the practice of this invention are given in the examples which follow, in which parts and percentages are by weight and solutions or suspensions are aqueous, unless otherwise indicated. Abbreviations used in the examples:

| | |
|---|---|
| Tris | tris(hydroxymethyl)aminomethane |
| EDTA | Ethylenediamine tetraacetic acid |
| 1X TEAc | 0.04 M Tris, 0.001 M EDTA, 0.01 M Sodium Acetate; pH 7.8 |
| Tris saline | 10 mM Tris-HCl, 0.9% Sodium Chloride; pH 7.4 |
| 0.1X SSC | .0015 M Sodium Citrate, .015 Sodium Chloride |
| 1X SSC | .015 M Sodium Citrate, .15 M Sodium Chloride |
| 2X SSC | .03 M Sodium Citrate, .3 M Sodium Chloride |
| 6X SSC | .09 M Sodium Citrate, .9 M Sodium Chloride |
| 10X SSC | .15 M Sodium Citrate, 1.5 M Sodium Chloride |
| 20X SSC | .3 M Sodium Citrate, 3.0 M Sodium Chloride |
| PVP | polyvinylpyrrolidone |
| BSA | bovine serum albumin |
| 1X Denhart's | 0.02% PVP (M.W. 40,000), 0.02% BSA, 0.02% Ficoll (M.W. 400,000) |
| 20X Denhart's | 0.4% PVP, 0.4% BSA, 0.4% Ficoll |
| SDS | sodium dodecyl sulfate |
| 10X MOPS | 0.2 M 3-[N—Morpholine]propanesulfonic acid, 0.05 M Sodium Acetate, 0.01 M EDTA; pH 7.0 |
| φX 174 | bacteriophage φX 174 |
| pBR322 | plasmid BR322 |
| HpaI | restriction endonuclease from *Haemophilus parainfluenza* |
| Pol I | DNA polymerase I |
| DNase I | Deoxyribonuclease I |
| 2X SET | 3 M NaCl, 0.02 M EDTA, 0.6 M Tris HCl; pH 8.0 |
| 5X SET | 7.5 M NaCL, 0.05 M EDTA, 1.5 M Tris HCl; pH 8.0 |
| 10X ExB | 0.5 M imidazole, pH 6.6, 0.045 M DTT, 0.1 M MgCl$_2$, 0.003 M MADP |
| 1X ELB | 0.04 M Tris, 0.01 M Sodium Acetate, 0.001 M NaEDTA, pH 7.8 |
| 20X ELB | 0.8 M Tris, 0.2 M Sodium Acetate, 0.02 M NaEDTA, pH 7.8 |
| DTT | Dithiothreitol |
| ADP | Adenosine Diphosphate |
| PNK | Polynucleotide Kinase |

EXAMPLE I

This exemplifies transfer of electrophoretically separated DNA fragments from an agarose electrophoresis gel to a porous nylon membrane by blotting.

1. Adjacent lanes of a 1% agarose slab electrophoresis gel were loaded with 0.5, 0.25 and 0.1 μg, respectively, of DNA fragments prepared by digestion of phage φX 174 replicative form DNA with HpaI restriction endonuclease.

2. The loaded gel was placed in an electrophoresis apparatus with 1× TEAc buffer and electrophoresed at 120 V and 190 mA for about 1 hour.

3. The gel was soaked for 20 minutes in aqueous ethidium bromide dye solution containing 250 μg of dye in 500 ml. of solution.

4. The gel was denatured by two 15-minute washes in 0.5N NaOH and 1M NaCl.

5. The gel was neutralized by two 30-minute washes in 0.5N Tris HCl buffer, pH 7.5, plus 3M NaCl.

6. Two pieces of Whatman 3 MM filter paper were wet with 20× SSC buffer and placed on a glass plate elevated over a tray of the buffer so that the ends of the paper extended into the buffer, forming wicks.

7. The gel was placed on top of the filter paper and a perspex bar was placed along each side of the gel.

8. A porous 66-nylon membrane (Pall Corp., Glen Cove, N.Y.), with bacterial filtration rating of 0.2μ, was cut to the exact size of the gel, soaked for 20 minutes in 20× SSC, and placed on the gel.

9. Five pieces of the same Whatman filter paper were cut to the same size as the gel and placed on top of the membrane.

10. A 2" stack of absorbent paper towels were cut to the same size as the gel and placed on top of the filter paper. Blotting was allowed to continue for about 12 hours. Paper towels were changed frequently and 20× SSC was added as needed.

11. The towels and top filters were removed, the gel and membrane were removed as a unit, and were then separated.

12. The membrane was washed in 2× SSC to remove agarose particles then dried at room temperature.

13. The membrane was baked at 70° C. for 3 hours in a vacuum oven.

14. The membrane was "prehybridized" by treating it with the following prehybridization buffer: 20× Denhart's solution plus 6× SSC and 0.5% SDS. (If desired, denatured salmon sperm DNA can be included. The purpose of the "prehybridization" is to fill the adsorptive sites of the nylon membrane, so that the radiolabeled DNA probe in the next step cannot be adsorbed by the nylon.)

15. The membrane was sealed in a plastic bag with 10 ml of 1× Denhart's solution containing 0.5% SDS, 6× SSC, 10% Dextran sulfate, 1 ml of 1 mg/ml denatured salmon sperm DNA, and 5.5 μg of radiolabeled denatured DNA probe ($4.36 \times 10^7$ dpm/μg) prepared by nick translation of φX 174 RF DNA using deoxythymidine 5'-tris-phosphate [methyl, 1',2'-$^3$H] and the enzymes Pol I and DNase I. Hybridization was permitted to continue overnight with agitation at 60° C.

16. The membrane was washed one time for 30 minutes at 60° C. in the above prehybridization buffer, two times for 30 minutes at 60° C. in 2× SSC and 0.1% SDS, and two times for 30 minutes in 2× SSC.

17. The membrane was air dried, sprayed with a liquid fluorography solution, and exposed to X-ray film at −80° C. for 27 hours. The resulting fluorogram showed that the DNA fragments had been transferred to and retained on the membrane.

18. The membrane was washed in ether for 5 minutes then in formamide for 60 minutes at 60° C. and then in fresh formamide for 30 minutes at 60° C. to remove the probe.

19. The membrane was washed 1 hour in the above prebybridization buffer.

20. Step 15 was repeated, except that the amount of probe was about 1.8 μg, the amount of denatured salmon sperm DNA was 2 μg, and hybridization was allowed to continue for 20 hours.

21. Steps 16 and 17 were repeated. The fluorogram showed that the DNA fragments had been retained on the membrane.

22. The membrane was washed 5 minutes in ether, then placed in 10% formamide in a shaking bath at 60° C. for 1 hour.

23. The membrane was dried, sprayed with a liquid fluorography solution, and exposed to X-ray film for 4 hours. The fluorogram showed that the radiolabeled probe had been removed.

EXAMPLE II

This exemplifies transfer of RNA from an acrylamide/agarose electrophoresis gel to a porous nylon membrane by electrophoresis (electroblotting).

1. An electrophoresis slab gel was prepared as follows. Agarose (0.35 g) was dissolved in about 40 ml water by boiling and the solution was cooled to 60° C. To the solution were added 7.5 ml of pH 7 10× MOPS buffer and 12.2 ml of 37% aqueous formaldehyde. The solution was stirred and 13.75 ml of a 30%, 24:1 mixture of acrylamide and N,N'-methylene-bis-acrylamide in water, 24 mg ammonium persulfate and 40 µl of N,N,N',N'-tetramethylenediamine were added. The mixture was poured onto a horizontal slab gel apparatus to provide a 5.5% acrylamide/0.5% agarose gel.

2. A sample for electrophoresis was prepared by mixing 2 µl of an aqueous solution of about 10 µg $E.$ $coli$ RNA, 12.2 µl of 37% aqueous formaldehyde, 7.5 µl of 10× MOPS buffer, and 53.3 µl of water, for a total 75 µl. The sample was incubated at 65° C. for 15 minutes, then 25 µl of a dye mix was added.

3. The sample was loaded onto the gel (10 µl per well) and subjected to electrophoresis for about 3 hours at 400 volts in 1× MOPS buffer.

4. The gel was washed 3 times in water, hydrolyzed in 50 mM NaOH for 30 minutes, then rinsed three times in 10 mM aqueous sodium borate, pH 9.2.

5. A porous nylon membrane with bacterial filtration rating of 0.2µ (AMF Inc.) was wet with 10 mM aqueous sodium borate, pH 9.2.

6. The gel and membrane were placed in an electrophoretic transfer device (a Hoefer Co. Transphor ® unit), and transferred by electrophoresis for 16 hours at 0.25–0.3 A in 10 mM aqueous sodium borate, pH 9.2, at 5° C. The current was increased to 1 A and electrophoresis continued for about 3 hours at 5° C.

7. The membrane was removed from the apparatus, rinsed in aqueous sodium borate, pH 9.2, air dried, and baked for 3 hours at 90° C. under vacuum.

8. The membrane was "prehybridized" by soaking it at 42° C. overnight in 50% formamide, 10× Denhart's solution, 3× SSC, and 0.5 mg/ml salmon sperm DNA.

9. The membrane was soaked at 42° C. for 48 hours in 50% formamide, 2× Denhart's solution, 3× SSC, 0.25 mg/ml (based on total solution) salmon sperm DNA and 25–50 ng/ml (based on total solution) of a $^{32}P$ hybridization probe prepared by nick translation of $E.$ $coli$ DNA using deoxycytidine 5'-triphosphate, [α-$^{32}P$] and the enzymes Pol I and DNase I, followed by denaturation.

10. The membrane was washed two times in 50% formamide, 5× SSC and 1% SDS at 42° C. for 30 minutes, then washed two times in 2× SSC and 1% SDS at 60° C. for 30 minutes.

11. The membrane was air dried and autoradiographed. The autoradiogram showed that the RNA was transferred to and retained on the membrane.

EXAMPLE III

This exemplifies transfer of protein from a gradient polyacrylamide electrophoresis slab gel to a porous 66-nylon membrane by electrophoresis and subsequent detection of the transferred protein by probing with an antibody linked to an enzyme.

1. A conjugate ($E_3$-BSA) of estriol ($E_3$) and bovine serum albumin (BSA) (conjugated at the 6-position of the estriol) was mixed with water at three different concentrations and loaded onto a 7.5–15% gradient polyacrylamide slab gel to provide 10, 20 and 40 µg $E_3$-BSA in lanes 2, 3 and 4, respectively, and also in lanes 6, 7 and 8, respectively. Lanes 1 and 5 were loaded with a mixture of molecular weight markers.

2. The gel was subjected to electrophoresis for 3–4 hours at 0.2 to 0.25 A.

3. The gel was removed from the electrophoresis apparatus and divided into two halves, A & B, between lanes 4 and 5. Part A was stained to detect proteins using Coomassie Brilliant Blue, destained and dried.

4. Part B of the gel was placed in an electrophoretic transfer device of the type used in Example II along with a porous 66-nylon membrane of the type used in Example II, and a solution of Tris 20 mM, glycine 150 mM and 20% methanol.

5. The gel and membrane were subjected to electrophoresis for 3½ hours at 0.2 A to transfer the $E_3$-BSA from the gel to the membrane.

6. To verify transfer, part B of the gel was stained, destained and dried as in step 2.

7. The membrane was incubated in Tris saline containing 5% BSA.

8. The membrane was incubated for 90 minutes at room temperature on a rocking platform in Tris saline containing 5% BSA and a mouse monoclonal antibody to estriol diluted to 1:100.

9. The membrane was washed with rocking for 10 minutes in 200 ml Tris saline, then washed twice for 20 minutes each time in 200 ml of Tris saline containing 0.05% of detergent NP-40 (Particle Data Laboratories, Ltd., Elmhurst, Ind.), then washed again for 10 minutes in 200 ml of Tris saline without BSA.

10. The washed membrane was immersed in Tris saline containing 5% BSA and 1:100 dilution of a goat-anti mouse antibody conjugated to Horse Radish Peroxidase (New England Nuclear Product NEI 501). Binding of the labeled goat antibody was allowed to proceed for 30 minutes at room temperature with rocking. The membrane was washed repeatedly as described in step 9.

11. The membrane was immersed in a fresh solution of 0.03% hydrogen peroxide, 3,3'-diaminobenzidine (1 mg/ml) and imidazole (1 mg/ml). The insoluble enzyme reaction products formed on the membrane revealed characteristic bands at the molecular weight points which represent the monomer, dimer, and trimer of the BSA molecule, indicating that the BSA had been transferred to and retained by the nylon membrane.

EXAMPLE IV

This exemplifies transfer of bacterial colonies from growth medium plates to a porous 66-nylon membrane.

1. Four agar plates, each containing 50–200 colonies of pBR 322 transformed $E.$ $coli,$ were provided.

2. A laminate comprising a polyester core between two layers of 66-nylon membrane with a bacterial filtration rating of 0.2µ (Pall Corp., Glen Cove, N.Y.), was placed on each plate and allowed to stand for 3 minutes, then carefully removed with flat-tipped forceps.

3. Each membrane was placed colony-side up on 0.75 ml pools of 0.5M NaOH for 2 minutes, then blotted with paper towels. This was repeated one time. This step produces cell lysis and denatures the pBR 322.

4. Each membrane was placed on a 0.75 ml pool of 1.0M Tris HCl, pH 7.5 for 2 minutes to neutralize it, then blotted with paper towels. This was repeated once.

5. Each membrane was placed on a 0.75 ml pool of 1.5M NaCl and 0.5M Tris HCl, pH 7.5, for 2 minutes, then blotted with paper towels. This was repeated once.

6. The membranes were dried and baked at 80° C. in vacuum for about 2 hours.

7. The membranes were agitated at 60° C. overnight with 20 ml of 5× Denhart's solution containing 100 μg/ml of denatured salmon sperm DNA.

8. The membranes were agitated at 60° C. for about 20 hours in 20 ml of 5× SET, 1× Denhart's, 1% SDS, 100 μg/ml of denatured salmon sperm DNA and about 50 ng/ml of denatured $^{32}$P hybridization probe prepared by nick translation of pBR 322 DNA using deoxycytidine 5'-triphosphate, [α-$^{32}$P] and the enzymes Pol I and DNase I.

9. The membranes were washed two times for 5 minutes at room temperature in 100 ml of 2× SET, two times for 60 minutes at 60° C. in 100 ml of 2× SET containing 0.5% SDS, and two times for 30 minutes at room temperature in 100 ml of 3 mM Tris base.

10. The membranes were air dried, wrapped in plastic film and exposed at −70° C. for 1 hour to X-ray film using a fluorescent intensifying screen. The resulting autoradiogram showed that the bacterial colonies were transferred to the nylon membranes and plasmid (pBR 322) DNA had been immobilized on the nylon surface.

EXAMPLE V

This exemplifies transferring $^{32}$P-labeled DNA from an agarose gel by capillary transfer to a positively charged porous 66-nylon membrane.

1. Ten μl Hinf 1 digest of *E. coli* plasmid DNA pBR 322 (5 μg), 2 μl 10× ExB (exchange buffer) 5 μl PNK (5 units), 3 μl H$_2$O and 0.15 nM $^{35}$P-ATP (dried) are mixed together in a test tube and incubated at 37° C. for 1 hour. The mixture was then heated to 65° C. for 10 minutes to kill PNK. Fifty μl 0.1M EDTA, 50 μl 1M sodium acetate (pH 5) and 700 μl cold ethanol are then added to the mixture. The test tube containing the mixture is placed in a dry ice/ethanol bath for 5 minutes and then centrifuged at 12,000×g for 5 minutes. The supernatant liquid is removed with a pipette. Seven hundred μl of cold ethanol are added to the resulting pellet and vortexed. The test tube is placed in dry ice/ethanol bath for 5 minutes, centrifuged at 12,000×g for 5 minutes and then the supernatant liquid removed with a pipette. The resulting pellet is dissolved in 85 μl of 20× ELB (electrophoresis buffer) containing a tracking dye.

2. A 2% agarose gel is prepared by dissolving 2 g agarose in 100 ml of 1× electrophoresis buffer heated to boiling followed by cooling the solution to 60° C. The gel is poured immediately and placed into a stand.

3. A buffer chamber having 6 wells is filled with 1× ELB (electrophoresis buffer). Twelve μl of $^{32}$P-labeled Hinf 1 digest of pBR 322 is applied to each of the 6 wells. The buffer chamber is electrophoresed at 100 v (35 mA) for about 5 minutes, after which the voltage is reduced to 40 v (11 mA) and kept at this level for 8 hours. The gel prepared in (2) is incubated in a 1 μg/1 ml solution of ethidium bromide/1× ELB (electrophoresis buffer) for 30 minutes to "stain" DNA. The gel is photographed under UV (300 nm) through an orange filter.

4. The gel is incubated in 0.4N sodium hydroxide—0.8M sodium chloride for 30 minutes to denature DNA. Then the gel is incubated in 1.5M sodium chloride—0.5M Tris-buffered to pH 7.6 with HCl for 30 minutes to neutralize the gel.

5. Two pieces of Whatman paper to be used as wicks are wet in 10× SSC. A 4.5 cm×17.5 cm strip of positive charge modified Zetapore ®, nylon 66, having a bacterial filtration rating of 0.2 μm membrane (AMF Cuno Division, 400 Research Parkway, Meridian, Conn.), a 4.5 cm×17.5 cm strip of an AMF uncharged nylon 66 membrane having a bacterial filtration rating of 0.2 μm and a 4.5×17.5 cm strip of an uncharged nylon strip having a bacterial filtration rating of 0.2 μm are wet in 10× SSC. An elevated glass plate is placed in a try with 1 liter of 10× SSC. Whatman filter papers are placed on the elevated glass plate such that each end of the papers is in the 10× SSC in the tray. The neutralized gel prepared above is placed on the wicks and 2 plastic spacers are placed on each side of the gel. The three membrane strips are placed on top of the gel, side-by-side. Six pieces of dry Whatman paper (15×17 cm) are placed on top of the membranes. Between one and two inches of paper towels (15×17 cm) are placed on top of the Whatman paper. A glass plate is placed on the towels to weigh them down. The blotting is continued for 20 hours, while changing the towels frequently. More 10× SSC is added as needed.

6. The strips are removed from set-up and dried under a heat lamp. Then the strips are baked at 90° C. for 3 hours under vacuum. Autoradiographs of the membranes are developed. The gel is incubated in a 1 μg/ml solution of ethidium bromide/1× ELB for 30 minutes. The gel is photographed under UV (300 nm) through an orange filter.

7. The membranes are mock hybridized and washed by first cutting each strip in half. Each of the half strips is aligned with the autoradiograph and from each strip is cut the following bands:

I. 1631 BP
II. 517-298 BP
III. 221-75 BP

All of the I's are placed in one scintillation vial, all the II's in one scintillation vial, and all the III's in one scintillation vial. Ten ml of Aquasol, a scintillation cocktail (NEN) are added to each vial and then counted in a scintillation counter. Divide dpm (disintegration per minute) by 3 and use as standard for each section. The remaining half of each strip is placed into a shallow tray. One hundred ml of 50% formamide, 5× SSC, 50 mM sodium phosphate, pH 6.5, 50 μg/ml salmon sperm DNA and 1× Denhart's are added to the tray. The contents of the tray are incubated at 42° C. for 2 hours with constant agitation. The solution in the tray is poured off and 10 ml of 1× SSC are added. The contents of the tray are incubated at room temperature for 1 hour with agitation. The strips are dried under a heat lamp. Each strip is cut into three bands I, II and III as described above in this paragraph. Each section (I, II, III) of each strip is placed into a separate vial, 10 ml Aquasol added and counted in scintillation counter.

8. The dpm obtained for each section (I, II, III) of each membrane is divided by the standard for that section and multiplied by 100 to obtain percentage of dpm that remained bound after mock hybridization and wash. DNA had been transferred and retained by the membranes. All three membranes performed similarly.

EXAMPLE VI

This example utilizes the Southern blotting technique and subsequent hybridization of transferred DNA using a positively charged nylon membrane.

1. DNA Transfer

An agarose gel is denatured with an aqueous solution of 0.2N NaOH and 0.6M NaCl which is gently agitated at room temperature for 30 minutes. The gel is neutralized with an aqueous solution of 0.5M Tris-HCl pH 7.6, 1.5M NaCl which is gently agitated at room temperature for 30 minutes. Two pieces of filter paper (Whatman 3 MM) are wet with 6× SSC and placed over elevated glass plate over a tray containing 6× SSC so that ends form wicks. The gel is placed on top of the filter paper and a perspex bar is placed along each side of the gel. A nylon 66 membrane having a 0.2 μm bacteria filtration rating is cut to exact size of the gel. The membrane is cut while between liner sheets with the operator wearing gloves. The membrane is soaked in 6× SSC for 15-20 minutes prior to placing on gel. Five pieces of Whatman filter paper cut to the same size as the gel is placed on top of the membrane. About a 1½" (3.8 cm) stack of absorbent paper towels, cut to the same size as the gel, is placed on top of the filter paper. Transfer is continued for 12 hours. The paper towels are changed frequently. More 6× SSC buffer is added as needed. The towels and Whatman filters are carefully removed without disturbing the membrane. The gel and membrane are removed as a unit from the wicks. Lanes are marked off with a pencil. The gel is flipped over onto a clear plastic wrap and carefully lifted off the membrane with the operator wearing gloves. The gel is stained and photographed to ensure efficient transfer. The membrane is washed carefully with 1× SSC by gently rubbing to remove residual agarose (Important: Residual agarose on membrane will lead to background problems). The membrane is patted dry with soft paper wipes and dried at room temperature. The DNA is baked onto the membrane at 80°-100° C. for 2-4 hours in a vacuum oven.

2. Hybridization

The membrane is prehybridized by treatment with 10 ml of the following solution: 0.2% polyvinyl-pyrrolidone (M.W. 40,000), 0.2% bovine serum albumin, 0.2% ficoll (M.W. 400,000), 0.05M Tris-HCl, pH 7.5, 1M NaCl, 0.1% sodium pyrophosphate, 1.0% SDS, 10% dextran sulfate (Pharmacia M.W. 500,000), and denatured salmon sperm DNA (100 μg/ml). The solution is added to a sealable plastic bag containing the membrane. The plastic bag is sealed and incubated at 60° C. with constant agitation for 6 hours.

About 2½ mls of the following solution is added to the bag containing the prehybridization buffer and membrane: 0.2% polyvinyl-pyrrolidone (M.W. 40,000), 0.2% bovine serum albumin, 0.2% ficoll (M.W. 400,000), 0.05M Tris-HCl, pH 7.5, 0.1% sodium pyrophosphate, 1.0% SDS, denatured salmon sperm DNA (100 μg/ml) and a radioactive probe. The plastic bag is sealed and incubated with constant agitation at 60° for about 20 hours.

The hybridization solution is removed and the membrane is washed as follows:

a. Twice with 100 ml of 2× SSC at room temperature for 5 minutes with constant agitation.

b. Twice with 100 ml of a solution containing 2× SSC and 1.0% SDS at 65° C. for 30 minutes with constant agitation.

c. Twice with 100 ml of 0.1× SSC at room temperature for 30 minutes with constant agitation.

The membranes are air dried, wrapped in plastic film and exposed at −70° C. for one hour to X-ray film using a fluorescent intensifying screen. The resulting autoradiogram shows that the DNA fragments had been transferred to and retained on the membrane.

It should be apparent from the examples shown here with radio- and enzyme-labeled probes that a wide variety of detection systems can be utilized with the current invention.

We claim:

1. In methods for transferring nucleic acids, proteins, bacteria or viruses from gel or culture media to a microporous adsorptive membrane, the improvement which comprises using as the membrane a microporous adsorptive nylon membrane.

2. Method of claim 1 wherein nucleic acids or proteins are transferred from an electrophoresis gel to a microporous adsorptive nylon membrane.

3. Method of claim 2 wherein the transfer is accomplished by blotting.

4. Method of claim 2 wherein the transfer is accomplished by electroblotting.

5. Method of claim 1, 2, 3 or 4 in which the membrane is a microporous 66-nylon membrane.

6. Method of claim 2, 3 or 4 wherein denatured DNA is transferred to the membrane and hybridized on the membrane with a labeled denatured DNA probe.

7. Method of claim 6 wherein the probe is removed by denaturation and the transferred DNA is rehybridized on the same membrane with another labeled DNA probe.

8. Method of claim 4 wherein RNA is transferred to the membrane and hybridized on the membrane with a labeled denatured DNA probe.

9. Method of claim 1 wherein nucleic acids, proteins, bacteria or viruses are transferred from a culture medium by contacting the medium with a microporous nylon membrane.

10. Method of claim 9 wherein bacteria are lifted from a colony in a culture medium by contact with a microporous 66-nylon membrane laminated to a support sheet.

* * * * *